(12) United States Patent
Jenkins

(10) Patent No.: US 6,606,523 B1
(45) Date of Patent: Aug. 12, 2003

(54) GASTRIC STIMULATOR APPARATUS AND METHOD FOR INSTALLING

(75) Inventor: David A. Jenkins, Flanders, NJ (US)

(73) Assignee: Transneuronix Inc., Mt. Arlington, NJ (US)

(*) Notice: Subject to any disclaimer, the term of this patent is extended or adjusted under 35 U.S.C. 154(b) by 0 days.

(21) Appl. No.: 09/466,532

(22) Filed: Dec. 17, 1999

Related U.S. Application Data

(60) Provisional application No. 60/129,198, filed on Apr. 14, 1999.

(51) Int. Cl.[7] ................................................ A61N 1/05
(52) U.S. Cl. ...................... 607/133; 607/116; 128/899; 600/393
(58) Field of Search ................................ 607/115, 116, 607/119, 124, 126, 127, 128, 129, 130, 131, 132, 133, 149, 152; 600/373, 375, 377, 393, 380; 128/899

(56) References Cited

U.S. PATENT DOCUMENTS

| | | | | |
|---|---|---|---|---|
| 2,536,271 A | * | 1/1951 | Fransen | 607/152 |
| 3,543,761 A | * | 12/1970 | Bradley | 607/40 |
| 3,646,940 A | * | 3/1972 | Timm et al. | 607/40 |
| 4,270,549 A | * | 6/1981 | Heilman | 607/129 |
| 4,379,462 A | | 4/1983 | Borkan et al. | 607/117 |
| 4,459,989 A | | 7/1984 | Borkan | 607/60 |
| 4,612,934 A | | 9/1986 | Borkan | 607/62 |
| 4,793,353 A | | 12/1988 | Borkan | 607/60 |
| 4,841,966 A | * | 6/1989 | Hagen et al. | 128/908 |
| 4,869,225 A | * | 9/1989 | Nagata et al. | 123/509 |
| 5,010,895 A | * | 4/1991 | Maurer et al. | 607/138 |
| 5,143,090 A | * | 9/1992 | Dutcher et al. | 607/121 |
| 5,154,182 A | * | 10/1992 | Moaddeb | 607/120 |
| 5,154,183 A | * | 10/1992 | Kreyenhagen et al. | 600/375 |
| 5,199,430 A | * | 4/1993 | Fang et al. | 607/118 |
| 5,292,344 A | | 3/1994 | Douglas | 607/40 |
| 5,342,413 A | * | 8/1994 | Hirschberg et al. | 607/126 |
| 5,391,200 A | * | 2/1995 | KenKnight et al. | 600/374 |
| 5,411,546 A | * | 5/1995 | Bowald et al. | 607/126 |
| 5,423,872 A | | 6/1995 | Cigaina | 607/40 |
| 5,464,447 A | * | 11/1995 | Fogarty et al. | 600/374 |
| 5,509,924 A | * | 4/1996 | Paspa et al. | 607/5 |
| 5,690,691 A | | 11/1997 | Chen et al. | 607/40 |
| 5,716,392 A | | 2/1998 | Bourgeois et al. | 607/132 |
| 5,836,994 A | | 11/1998 | Bourgeois | 607/40 |
| 5,846,196 A | * | 12/1998 | Siekmeyer et al. | 600/374 |
| 5,861,014 A | | 1/1999 | Familoni | 607/40 |
| 5,995,872 A | | 11/1999 | Bourgeois | 607/40 |
| 6,296,630 B1 | * | 10/2001 | Altman et al. | 604/508 |

FOREIGN PATENT DOCUMENTS

WO   WO 99/03532   1/1999   ............ A61N/1/36

OTHER PUBLICATIONS

B. Bellahsene, et al., "Evaluation of a Portable Gastric Stimulator," *Proceedings of the Ninth Annual Conference of the IEEE Engineering in Medicine and Biology Society*, Nov. 1987, pp. 1652–1653.

(List continued on next page.)

*Primary Examiner*—Kennedy Schaetzle
(74) *Attorney, Agent, or Firm*—Fitch, Even, Tabin & Flannery

(57) ABSTRACT

Apparatus for stimulating neuromuscular tissue of the gastrointestinal tract and methods for installing the apparatus to the surface of the neuromuscular tissue. A pair of electrodes are supported by an electrode attachment member having a distal surface configured for attachment to the surface of the neuromuscular tissue. The electrodes are supported adjacent the distal surface to provide an interface between the electrodes and the surface of the neuromuscular tissue. The electrode attachment member may be flexible to pass through a laparoscopic surgical access opening in a compacted form and then returned to an uncompacted form for attachment to the surface of the neuromuscular tissue by the use of staples or sutures.

10 Claims, 7 Drawing Sheets

OTHER PUBLICATIONS

B. Bellahsene, "Effects of Gastric Electrical Stimulation (Pacing) as Measured Through Gastric Emptying and Electrogastrograms," *Dissertation Abstracts International*, vol. 50/02–B, 1988, p. 658.

J.D. Chen, et al., "Long–Term Gastric Pacing with a Portable Gastric Pacemaker to Aid Gastric Emptying in Humans," *Proceedings of the 1995 IEEE Engineering in Medicine and Biology 17th Annual Conference*, Sep. 1995, pp. 1691–1692.

J.D. Chen, et al., "Gastric Electrical Stimulation in Patients with Gastroparesis," *Journal of Gastroenterology and Hepatology, Proceedings of the Alimentary Disease Week*, Dec. 1997, pp. S232–S236.

S.D. Jundler, "An Electronic Pacemaker for the Electrical Control Activity of the Stomach," *Masters Thesis, Institute of Biomedical Engineering, University of Toronto*, Mar. 1991.

K.A. Kelly, "Differential Responses of the Canine Gastric Corpus and Antrum to Electrical Stimulation," *American Journal of Physiology*, vol. 226, No. 1, Jan. 1974, pp. 230–234.

L.J. Levien, "The Response of the Canine Stomach to Stimulatory and Inhibitory Vagal Nerve Activity," *Dissertation Abstracts International*, vol. 41/08–B, 1980, p. 2915.

M. Mintchev, et al., "Computer Model of Gastric Electrical Stimulation," *Annals of Biomedical Engineering*, vol. 25, No. 4, 1997, pp. 726–730.

S. Xue, et al., "Electrical Slow Wave Activity of the Cat Stomach: Its Frequency Gradient and the Effect of Indomethacin," *Neurogastroenterology and Motility*, vol. 7, No. 3, Sep. 1995, pp. 157–167.

N.B. Halpern, et al., "Effects of Partitioning Operations on the Electrical Activity of the Human Stomach," *Journal of Surgical Research*, vol. 32, No. 3, Mar. 1982, pp. 275–282.

R.L. Telander, et al., "Human Gastric Atony with Tachygastria and Gastric Retention," *Gastroenterology*, vol. 75, No. 3, Sep. 1978, pp. 497–501.

"Research at the Center for Semicustom Integrated Systems", University of Virginia, Internet website: http://csis.ee.virginia.edu/research/research.html, Jun. 5, 1998.

\* cited by examiner

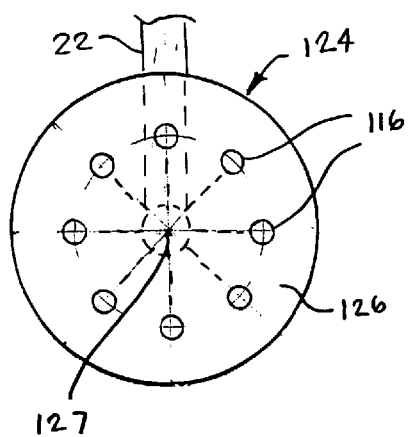
FIG. 4
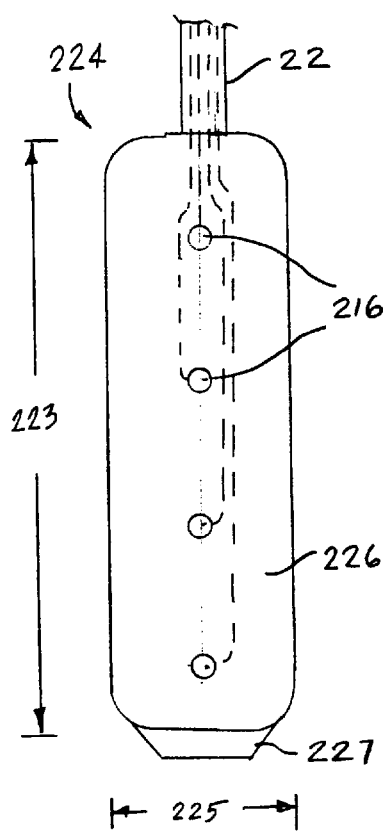
FIG. 5
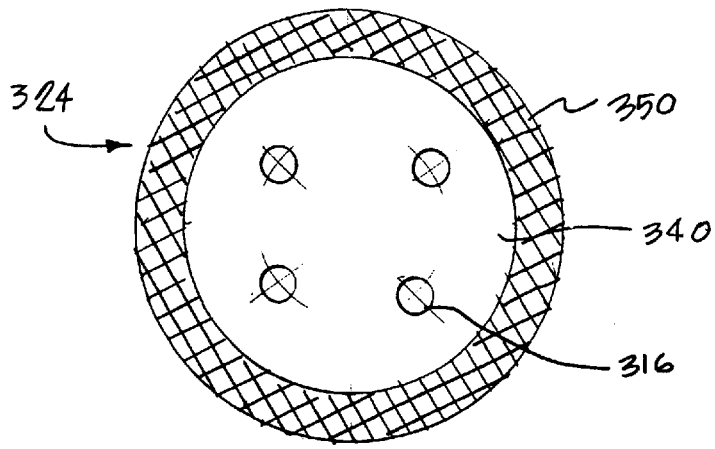
FIG. 6
FIG. 7
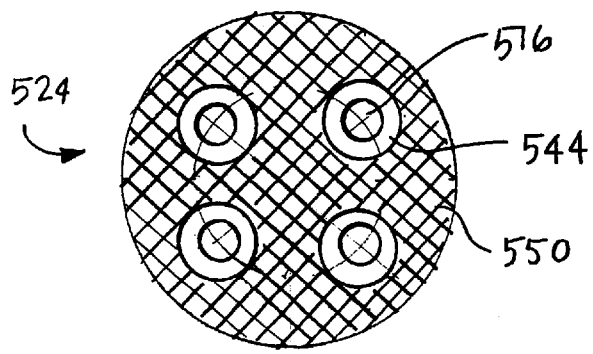
FIG. 8

GASTRIC STIMULATOR APPARATUS AND METHOD FOR INSTALLING

This application claims the benefit of U.S. Provisional application Ser. No. 60/129,198, filed Apr. 14, 1999, which is incorporated by reference in its entirety herein.

BACKGROUND OF THE INVENTION

This invention relates to electrical stimulation apparatus and methods for use in stimulating body organs, and more particularly to implantable apparatus for stimulating neuromuscular tissue of the viscera of the organ structure, including the gastrointestinal tract and methods for installing the apparatus in a patient.

The field of electrical tissue stimulation has recently been expanded to include devices which electrically stimulate the stomach or intestinal tract with electrodes implanted in the tissue. These gastric stimulators have been found to successfully combat obesity in certain studies. Medical understanding as to how this treatment functions to reduce obesity is currently incomplete. However, patients successfully treated report achieving normal cycles of hunger and satiation. Some evidence supports the theory that food passes through the body quicker when the stimulation is occurring.

U.S. Pat. No. 5,836,994 to Bourgeois describes a laparoscopic device which has a needle which passes through the tissue being stimulated, and a thread attached at one end to the needle and at the other end to an implantable pulse generator (IPG) lead. The entire device can be inserted into the body via a laparoscopic type tube, or trocar, as it is relatively long and narrow. Many devices are known to be inserted through a trocar by having a needle attached with a thread to the devices.

Copending Cigaina U.S. application Ser. No. PCT/US98/1042 filed on May 21, 1998, and copending Cigaina U.S. application Ser. No. 09/122,832, filed Jul. 27, 1998, now U.S. Pat. No. 6,041,258 both of which are incorporated by reference in their entirety herein, describe a novel apparatus wherein the needle is incorporated into the end of the lead. Once the electrodes are inserted into the viscera, the electrodes are fixed in place by reverse angle tines.

A potential disadvantage of the above apparatus and methods of installation is that the electrodes must be affixed to the muscle of the stomach by actually imbedding the electrodes inside the tissue. Such a procedure may occasionally result in accidental deep perforation of the viscera. For example, the stomach muscle wall is generally less than 1 cm in depth, and the surgeon could easily puncture the inner wall of the stomach by angling his needle too deeply.

Thus, there is a need to provide an electrode apparatus that reduces the risk of injury to viscera tissue.

It is an advantage to provide an apparatus and methods of stimulation wherein the risk of injury to the viscera is reduced.

It is a further advantage of this invention is to allow the electrodes to interface the tissue on the outside surface of the viscera.

It is also an advantage of the invention to provide an apparatus and methods of stimulation wherein the electrodes may be implanted in a minimally invasive manner, such as laparoscopically.

It is a further advantage of the invention to provide an apparatus and methods of installing an electrode, wherein the electrode and any attachment means may be reduced in size to a compact form for installation into the patient's body.

Summary of the Invention

These and other objects of the invention are accomplished in accordance with the principles of the invention by providing apparatus and methods for installing such apparatus to the surface of neuromuscular tissue of the viscera, and particularly, the gastrointestinal tract. The apparatus includes at least two stimulating electrodes electrically connected to a pulse generator that supplies electrical stimulating pulses to the neuromuscular tissue. An electrode attachment member supports the electrodes, which may be embedded or otherwise attached to the electrode attachment member. The electrode attachment member has a distal surface configured for attachment to the surface of the neuromuscular tissue. The electrodes are at least partially exposed at the distal surface to provide an interface between the electrodes and the neuromuscular tissue.

In the most preferred embodiment, the electrode attachment member has a substantially flat distal surface fabricated from a flexible material. This flexibility allows the distal surface to substantially conform to any curvature of the neuromuscular surface. The flexibility also permits the electrode attachment member to be reduced in size to a compact form by rolling, folding, etc. The electrode attachment member may be inserted into the patient while in the compact form through minimally invasive laparoscopic or similar surgical access openings. A cylindrical sleeve member or annular bands may be provided to surround the electrode attachment member to assist in maintaining it in the compact form.

Preferred methods for installation in accordance with the invention include providing an electrode and an electrode attachment member which supports the electrodes adjacent a distal surface thereof. A further step may include providing a surgical access opening in the patient and laparoscopically introducing the electrode and the electrode attachment member into the patient. A subsequent step may include attaching the electrode attachment member to the surface of the neuromuscular tissue to provide an interface between the electrode and the tissue.

According to a preferred embodiment, the methods may also include partially compacting the electrode attachment member prior to laparoscopically introducing it into the patient. The compacting of the electrode attachment member may be performed by rolling or folding the member. The method may also include retaining the electrode attachment member in the compact form, such as, e.g., inserting it into an introduction sleeve or surrounding it with one or more annular bands.

After passing the electrode attachment member into the patient, the method may include returning the electrode attachment to its uncompacted form. If an introduction sleeve has been used, the method may include removing the electrode attachment member from the introduction sleeve. According to another preferred embodiment, the method may include severing the introduction sleeve or the bands and allowing the electrode attachment member to return to an uncompacted configuration. The method may include attaching the electrode attachment member to the neuromuscular tissue by stapling or suturing.

Although electrode attachment members in the form of a patch are described above, certain aspects of the invention are equally applicable to electrodes and electrode attachment members having other shapes and other methods of installation.

Further features of the invention, its nature and various advantages will be more apparent from the accompanying drawings and the following detailed description of the preferred embodiments.

BRIEF DESCRIPTION OF THE DRAWINGS

FIG. 4 is a view similar to FIG. 2 of an alternative embodiment of the apparatus in accordance with the invention.

FIG. 5 is a view similar to FIG. 2 of another alternative embodiment of the apparatus in accordance with the invention.

FIG. 6 is a view similar to FIG. 2 of yet another alternative embodiment of the apparatus in accordance with the invention.

FIG. 7 is a view similar to FIG. 2 of still another alternative embodiment of the apparatus in accordance with the invention.

FIG. 8 is a view similar to FIG. 2 of another alternative embodiment of the apparatus in accordance with the invention.

DETAILED DESCRIPTION OF THE PREFERRED EMBODIMENTS

Figure 1:
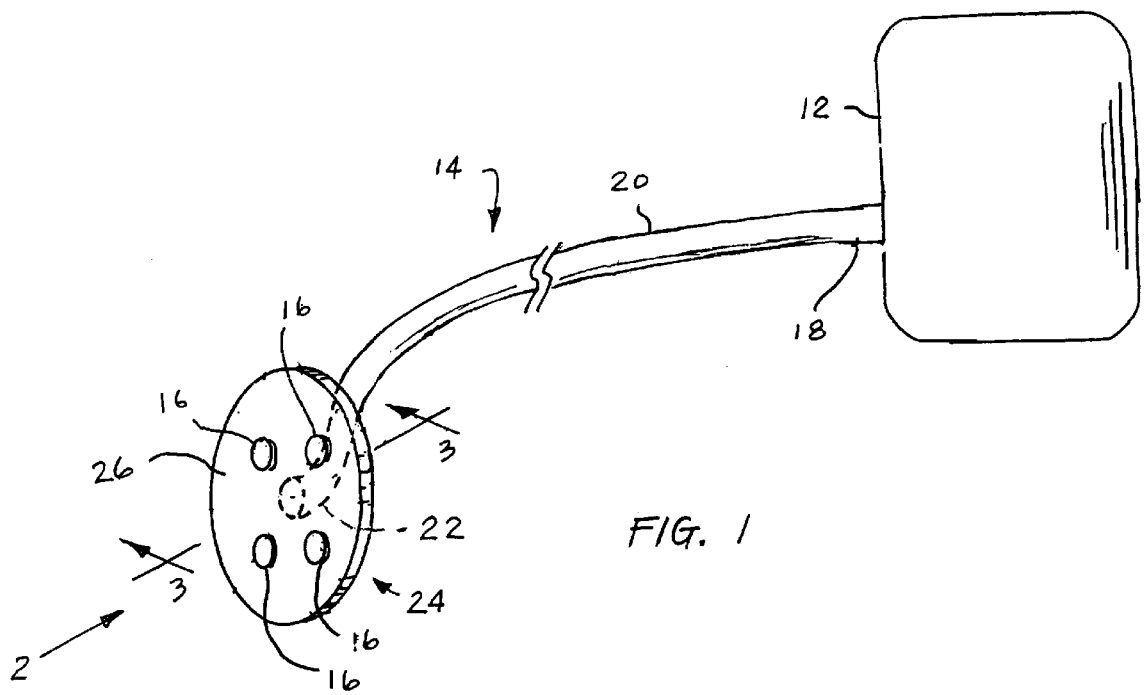
FIG. 1 is a simplified perspective view of a preferred embodiment in accordance with the invention.

An improved neuromuscular stimulator is illustrated in FIG. 1, and designated generally with reference number 10. The stimulator 10 includes an implantable pulse generator 12, a lead system 14 and two or more stimulation electrodes 16. The implantable pulse generator 12 provides a series of electrical pulses to the neuromuscular tissue of the viscera. It is understood that the viscera may include any organs of the abdominal region. For example, the principles in accordance with the invention are applicable to such body organs as the liver, pancreas, and the gastrointestinal tract (not shown in the FIG.). Suitable pulse generators, electrodes and electrode attachment members and stimulation techniques are described in commonly-assigned U.S. Pat. No. 5,423,872 to Cigaina, concurrently-filed Gordon U.S. Provisional Patent Application Ser. No. 60/129,209, and concurrently-filed Gordon U.S. Provisional Patent Application Ser. No. 60/129,199, all of which are incorporated by reference in their entirety herein. The implantable pulse generator 12 may be surgically implanted subcutaneously in the abdominal wall. The electrical stimulation lead 14 includes a proximal connector end 18 to interface with the implantable pulse generator 12, a medial lead body portion 20, and a distal end 22, for electrical connection with the electrode 16. The electrodes 16 are installed in contact with the surface of the stomach tissue, or other viscera. In a preferred embodiment, the electrodes 16 are supported an electrode attachment member 24, which may be attached to the stomach by sutures or staples. As will be described in greater detail below, the electrodes 16 and electrode attachment member 24 may be inserted to the body cavity laparoscopically through a trocar or other minimally invasive surgical access opening.

Figure 3:
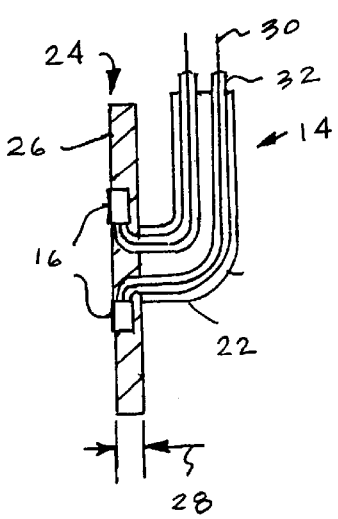
FIG. 3 is a simplified sectional view taken from line 3—3 of FIG.1 of a component of the apparatus in accordance with the invention.
Figure 2:
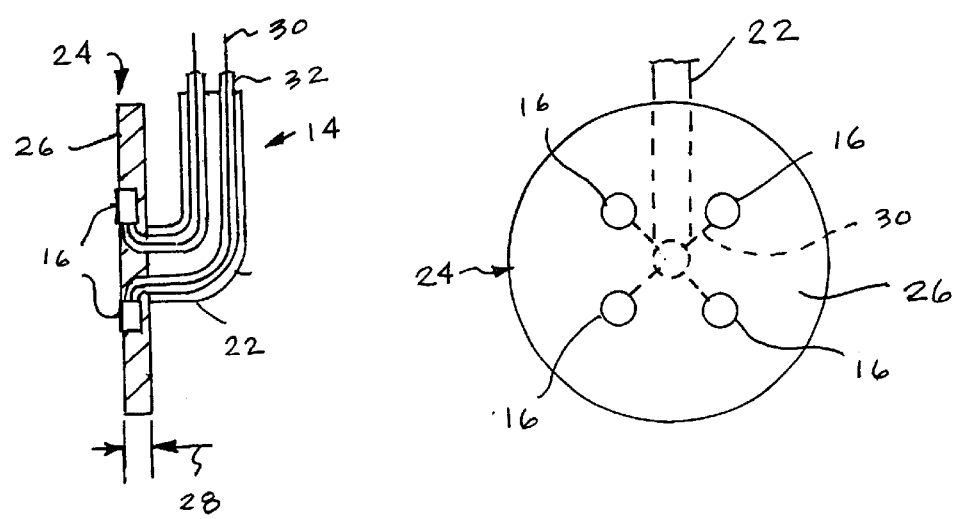
FIG. 2 is an elevational view taken from direction 2 of FIG. 1 of a component of the apparatus in accordance with the invention.

As illustrated in FIGS. 2 and 3, the stimulation electrodes 16 and the electrode attachment member, such as patch 24, are adjacent the distal end portion 22 of the lead 14. There may be several stimulation electrodes 16, fabricated from a metallic or other conductive material, attached to or partially embedded within the patch 24. The electrodes are exposed at the distal surface 26 of the patch 24, which may be attached to the surface of the tissue being stimulated.

The patch is provided with substantially flat distal surface 26, which shall generally refer to the configuration of the surface as relatively broad in relation to the thickness 28 or depth of the patch 24 as a whole. In a preferred embodiment, patch 28 has a diameter of, for example, about 1 to 3 cm and a thickness of, for example, about 3 to 5 mm. The distal surface 26 may be, e.g., substantially planar, curved, (e.g., convex, concave, or another appropriate curvature). Alternatively, the distal surface 26 may be flexible to conform to the surface of the tissue to which it is to be attached, etc. The electrodes 16 are supported by the patch 24, and positioned adjacent the distal surface 26 in order to provide an interface between the electrodes 16 and the surface of the tissue being stimulated. The interface between the electrodes 16 and the tissue being stimulated is sufficient to allow for the use of a low impedance stimulation.

The patch 24 may be constructed from a flexible material, such as, e.g., silicone elastomer or similar material. The base materials for the electrode 16 may include, e.g., platinum, platinum-iridium alloys, titanium and the like. The electrodes 16 may be in an uncoated state or may be coated with materials such as iridium oxide or titanium nitride, or the electrodes may be platinized or carbonized. In a preferred embodiment, the patch has a substantially circular configuration. It is understood that patch 24 may be fabricated in any suitable configuration, such as, for example, oval, square, rectangular, etc. The electrodes 16 may be distributed around the distal surface 26 substantially equidistantly or eccentrically from the center of the distal surface 26. For example, if an array of electrodes is being used for multiple stimulation vectors, and eccentric placement of the electrodes may be preferred to phase the stimulating pulses, and consequently the contractions.

Alternative embodiments of electrode attachment member 24 are illustrated in FIGS. 4 and 5. For example, FIG. 4 illustrates patch 124 having a plurality of electrodes 116 distributed substantially uniformly about the distal surface 126 thereof. More particularly, electrodes 116 are positioned substantially equidistantly about the center 127 of patch 124. FIG. 5 illustrates an alternative patch 224 having a substantially rectangular configuration wherein the length 223 is longer than the width 225. Electrodes 216 are distributed in a substantially linear configuration on the distal surface 226 of patch 224 to provide an interface with the tissue to which patch 224 is attached. A flap 227 is provided on patch 224 in order to provide a location for surgical instruments to grasp and manipulate patch 224, as will be described in greater detail below.

With continued reference to FIG. 3, the implantable electrical stimulation lead 14 includes a plurality of distinct conductors 30, each of which is connected electrically to a corresponding electrode or electrodes 16 on the distal end. The conductors may be surrounded by an electrically insulative material 32 to isolate the non-common conductors from each other, as necessary, and to isolate the conductor 30 from the physiological environment. The lead body 20 may include a plurality of conductive coils (not shown) isolated within an electrically insulative material such as silicone elastomer. The lead body 20 may utilize a coaxial or parallel conductor design. The conductive coils of the lead body shall electrically connect the proximal terminations of the lead to their corresponding distal electrode or electrodes 16.

With continued reference to FIG. 2, the patch 24 is constructed to allow attachment to the surface of the tissue being stimulated. In a preferred embodiment, the patch material is selected to allow sutures or staples to pass directly therethrough to permit the attachment to the tissue. Alternatively, it is contemplated that the patch may be provided with a plurality of pre-formed openings or apertures (not shown) to permit the passage therethrough of sutures or staples.

According to an alternative embodiment, the patch may be reinforced with a matrix of nylon or polyester mesh. As illustrated in FIG. 6, the mesh 350 may protrude from the edges of the body portion 340 of patch 324. (The body portion 340 is preferably fabricated from silicone elastomer.) Mesh 350 may serve as the anchoring or attachment surface for the sutures or staples. Alternatively, FIG. 7 illustrates that the mesh portions 450 may be exposed within the body 440 of the patch 424. In yet another alternative embodiment illustrated in FIG. 8, the electrodes 516 may be attached directly to a matrix of nylon or polyester mesh 550 allowing folding or rolling of the distal end. The mesh 550 is utilized as the attachment surface for the staples or sutures. The electrodes 516 may be embedded in small pads 544 of silicone elastomer, such that a portion of the electrodes 516 are exposed to provide the interface with the tissue being stimulated.

Figures 9A, 9B:
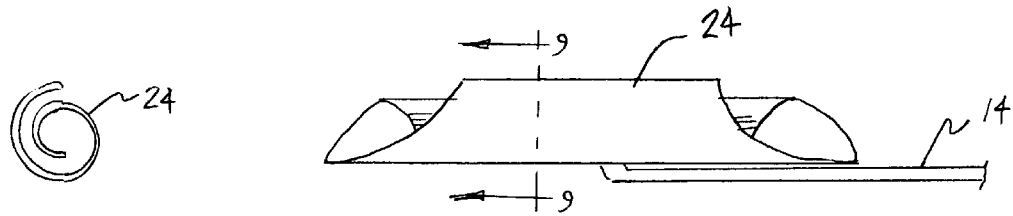
FIG. 9(a) is a simplified view of the apparatus of FIG. 2 in a compacted form in accordance with the invention.
FIG. 9(b) is a sectional view taken from line 9—9 of the apparatus of FIG. 9(a) in accordance with the invention.
Figures 10A, 10B:
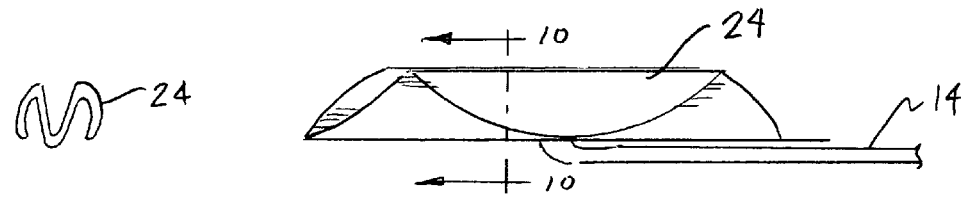
FIG. 10(a) is a simplified view of the apparatus of FIG. 2 in a compacted form in accordance with the invention.
FIG. 10(b) is a sectional view taken from line 10—10 of the apparatus of FIG. 10(a) in accordance with the invention.
Figures 11A, 11B:
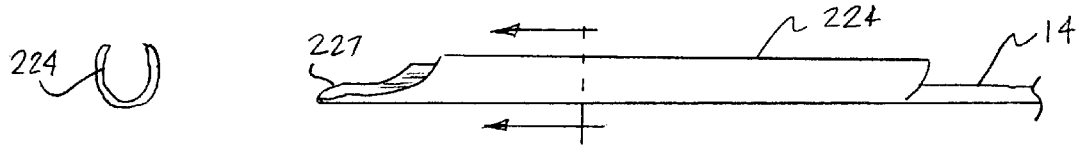
FIG. 11(a) is a simplified view of the apparatus of FIG. 2 in a compacted form in accordance with the invention.
FIG. 11(b) is a sectional view taken from line 11—11 of the apparatus of FIG. 11(a) in accordance with the invention.

According to the preferred embodiment, the patch is flexible. The flexibility of the patch permits the patch to be reduced to a compact form by rolling or folding. As illustrated in FIGS. 9(a)–(b), the patch 24 may be rolled into a compact form, having a substantially cylindrical configuration with a diameter of, for example, about 1 to 1.5 cm. FIGS. 10(a)–(b) illustrate patch 24 folded into a compact form. Elongated patch 224 may similarly be rolled or folded lengthwise into a compacted form, as shown in FIGS. 11(a)–(b).

Figure 12:
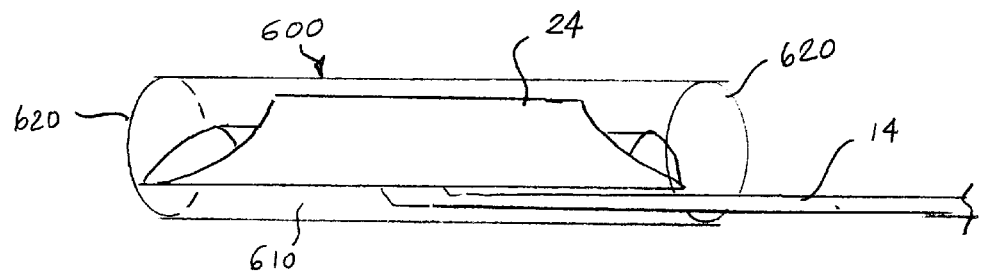
FIG. 12 is a simplified view of the apparatus of FIG. 9, illustrating additional apparatus in accordance with the invention.

The patch 24 may be inserted in a compact form into a patch holder, such as introduction sleeve 600 (FIG. 12). The introduction sleeve 600 may have a substantially cylindrical body portion 610 with first and second open end portions 620. Introduction sleeve 600 is sized and configured to permit introduction into the patient through a minimally invasive surgical access opening, such as a small incision or trocar device, etc. In a preferred embodiment, sleeve 600 has a diameter, for example, of about 1–1.5 cm for passage through a trocar having a diameter of about 1–2 cm.

The introduction sleeve 600 holds the patch while in the compact form. The sleeve 600 may be configured to allow a surgical device or similar device to remove the patch from the introduction sleeve 600 either by grasping and pulling the patch out of the sleeve, or by pushing the patch out of the sleeve. Alternatively, the sleeve 600 may be manufactured from a material sufficiently frangible such that a surgical device may be used to break or tear the sleeve to release the patch therefrom. The procedure for removing the patch from the sleeve is described in greater detail herein.

Figure 13:
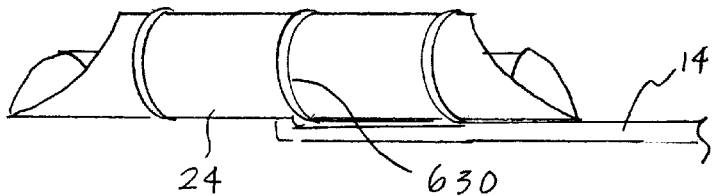
FIG. 13 is a simplified view of the apparatus of FIG. 9, illustrating additional apparatus in accordance with the invention.

According to an alternative embodiment, illustrated in FIG. 13, the patch 24 is placed in the compact form and is secured by securement bands, such as polyester bands or threads 630. During installation, the bands or threads may be released, e.g., by cutting, etc., after insertion through the trocar, as will be described in greater detail hereinbelow.

Installation of the Preferred Embodiment

Figure 14:
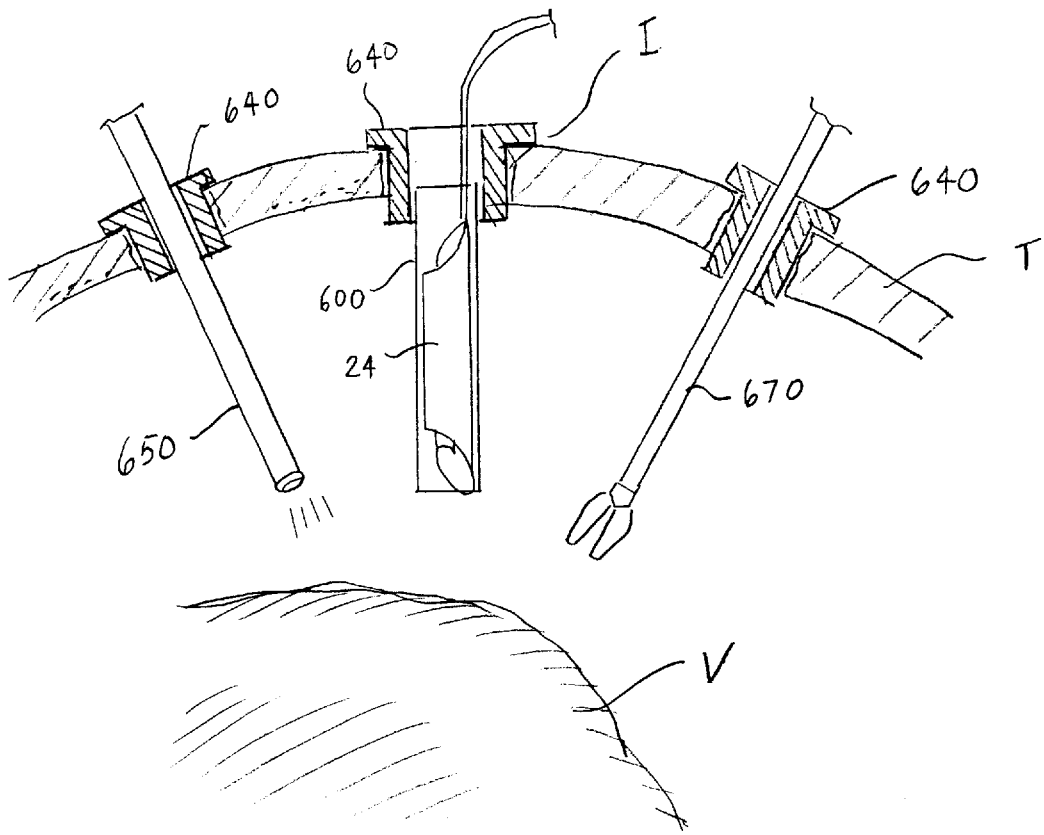
FIG. 14 is a simplified view in reduced scale and partially in section, illustrating an early stage in the process in accordance with the invention.

The above-described configuration of the electrodes and electrode attachment member provides for a simple, minimally-invasive installation procedure in accordance with the invention. According to an early stage of the invention illustrated in FIG. 14, the approximate location of the gastrointestinal tissue is located by the physician. An incision I is made in the patient in the surface of the skin above the operative site. According to a preferred embodiment, an obturator device (not shown) may be used to provide the incision and install a trocar. The process of insufflation may be used, wherein an inert gas such as carbon dioxide is introduced under pressure, to enlarge the body cavity and provide improved visualization and access within the body cavity. A series of trocars 640 may be installed through the patient's skin T which allow access for surgical instrumentation while maintaining insufflation pressure. A laparoscope 650 or similar remote viewing apparatus may be inserted through one of the trocars in order to allow viewing of the process of attachment of the electrode attachment member to the surface of the tissue, such as the stomach tissue V, in this example.

The electrode attachment member, e.g., patch 24 (or alternatively, patch 124, 224, 324, 424, or 524) is provided in compact form in the introduction sleeve 600 (see, FIG. 13). In the case of the electrodes positioned on the elongated electrode attachment member 224 (FIG. 5), the patch could be contained to a width of 1 cm or less. The distal patch 24 within sleeve 600 is passed through a trocar 640 as illustrated in the FIG. It is contemplated that sleeve 600 may be omitted when patch 24 is passed through the trocar or other access opening.

Figure 15:
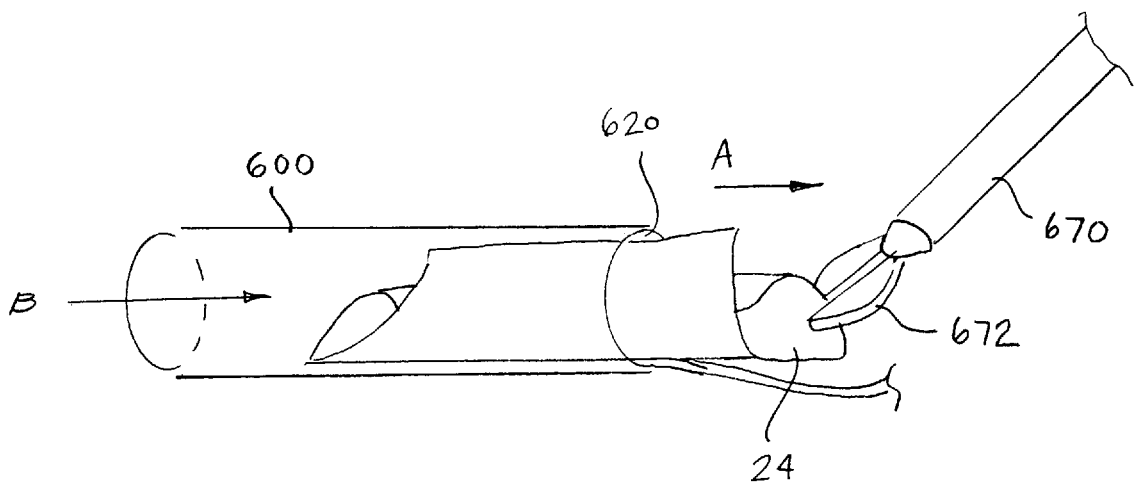
FIG. 15 is a simplified view, illustrating a later stage in the process in accordance with the invention.

After trocar passage, the patch 24 may be freed from the sleeve 600 by mechanical means, as illustrated in FIG. 15. For example, mechanical grasping apparatus, such as grasper 670, may be used to hold patch with grasping jaws 672 to remove patch 24 as indicated by arrow A from an end portion 620 of the sleeve 600. If elongated patch 224 is used, graspers 670 may be used to remove patch 224 from sleeve 600 by grasping flap 227 (See, FIGS. 5 and 11(*a*)). According to an alternative embodiment, the patch 24 is pushed out of sleeve 600 by advancing an apparatus in the direction indicated by arrow B by a blunt instrument (not shown), such as a plunger, a blunt dissection device, or a balloon catheter device.

Figure 16:
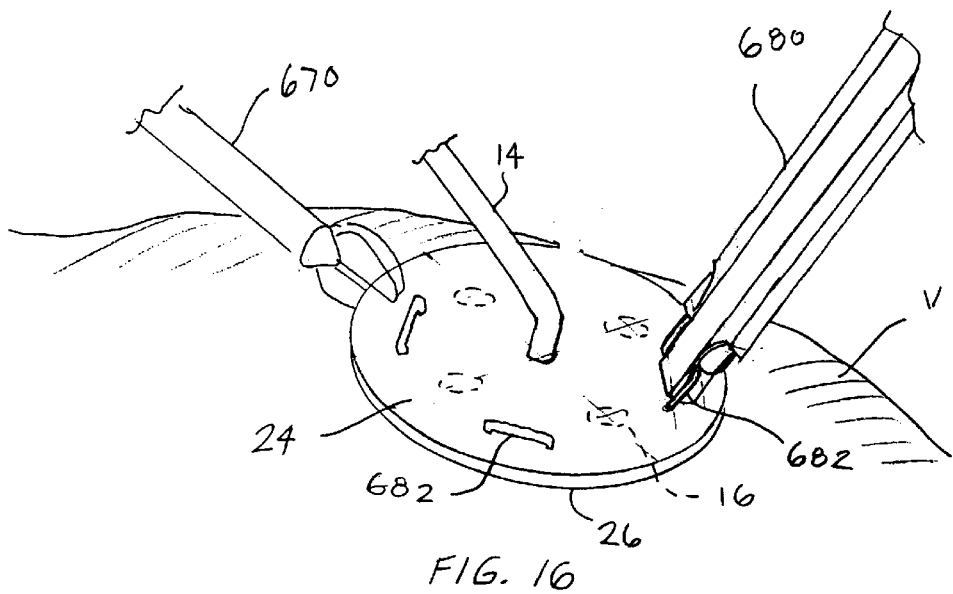
FIG. 16 is a simplified view illustrating a still later stage in the process in accordance with the invention.

The patch 24 is returned to its open, uncompacted form, as illustrated in FIG. 16. The grasper 670 may be used to position the patch 24 adjacent the surface of the viscera V of the stomach. More particularly, the distal surface 26 of the patch 24 is placed adjacent the tissue such that the exposed portions of the electrodes 16 are near the surface of the viscera in order to provide an interface between the electrodes and the surface of the gastrointestinal tissue. (See, FIG. 17) The interface is sufficient to allow for a low impedance stimulation. Typical impedances may range from about 300 to 800 ohms, with stimulating voltages in the range of 2.5 to 5.0 volts and stimulating currents in the range of about 4 to 6 milliamps. The voltages and currents are dependent upon the stimulating pulse widths and frequency.

Figure 17:
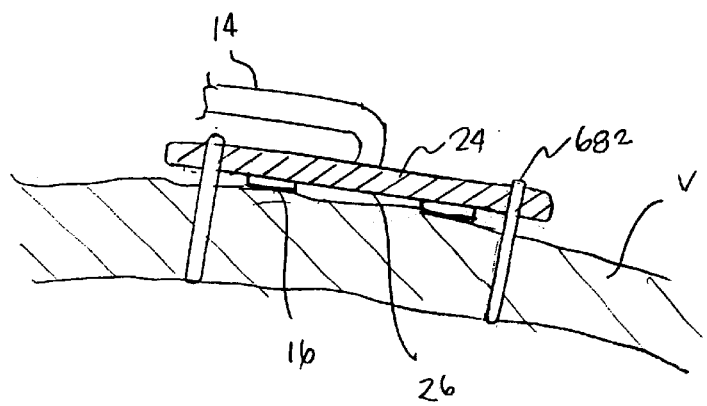
FIG. 17 is a sectional view illustrating the apparatus installed in accordance with the invention.

Attachment of the patch to the viscera may be achieved in several ways. As illustrated in FIG. 16, a stapling apparatus, such as endoscopic stapler or suture applying apparatus 680, may be used. Stapler 680, as is known in the art, may be sized and configured for insertion through the trocar or other minimally invasive surgical access opening, and remotely actuable by the physician. The stapler 680 applies at least one or more staples or sutures 682 to attach the patch to the viscera. The installed patch 24 is illustrated in FIG. 17. Distal surface 26 is illustrated in a substantially planar configuration. However, because patch 24 may be flexible, the distal surface 26 may curve to conform to the surface of the viscera V.

Figure 18:
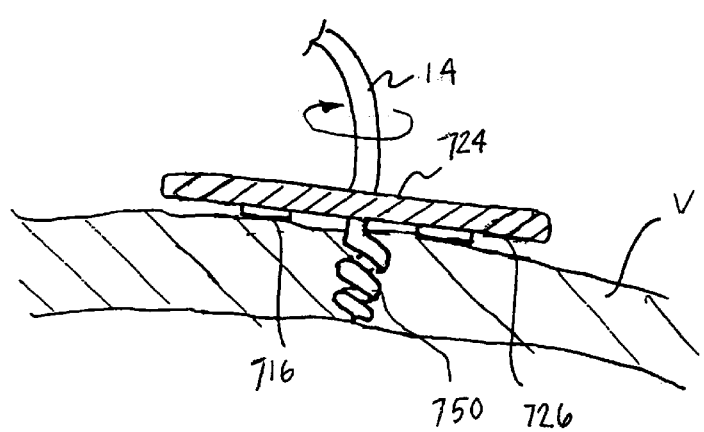
FIG. 18 is a view similar to FIG. 17, illustrating an alternative embodiment in accordance with the invention.

FIG. 18 illustrates an alternative embodiment of the apparatus in accordance with the invention. Electrode assembly 724 is substantially identical to electrode attachment member 24 described above with respect to FIGS. 1–4, with the differences noted herein. In particular, electrode assembly 724 is provided with a substantially helical or corkscrew-type attachment member 750 protruding from the distal surface 724 of the patch 724. In a preferred embodiment, helical attachment member 750 may also serve as an electrode for stimulating the neuromuscular tissue. The helical attachment member 750 may be easily applied to the tissue by rotating the electrode assembly 724 with respect to the tissue. Alternatively, the helical attachment member may be used to directly pierce the tissue S without rotation, such that the concentric rings of the helical attachment member 750 provide sufficient anchoring against removal of the electrode assembly 724 from the viscera V. Moreover, helical attachment member 750 maintains an interface between electrodes 716 and the surface of the viscera V.

Figure 19:
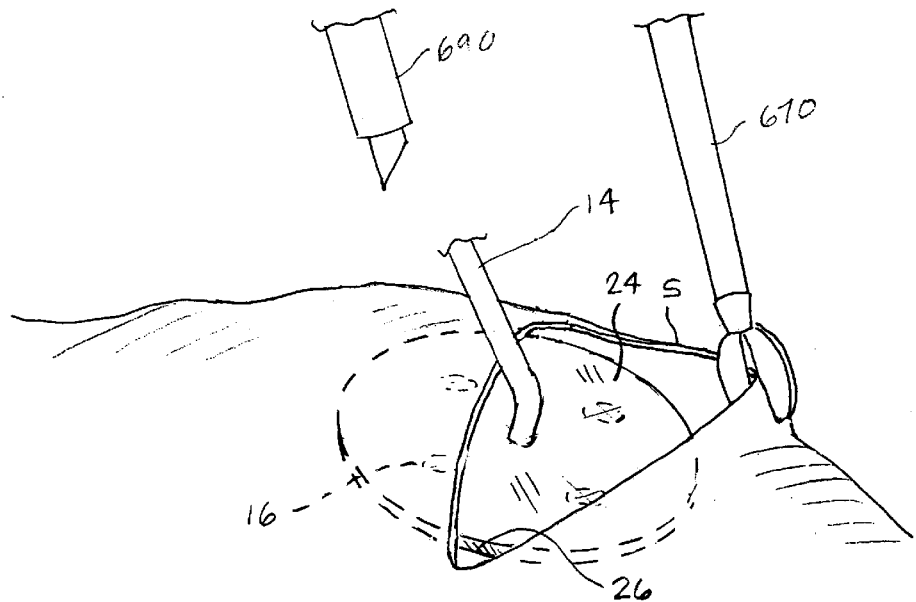
FIG. 19 is a simplified view illustrating a stage in an alternative embodiment of the invention.
Figure 20A:
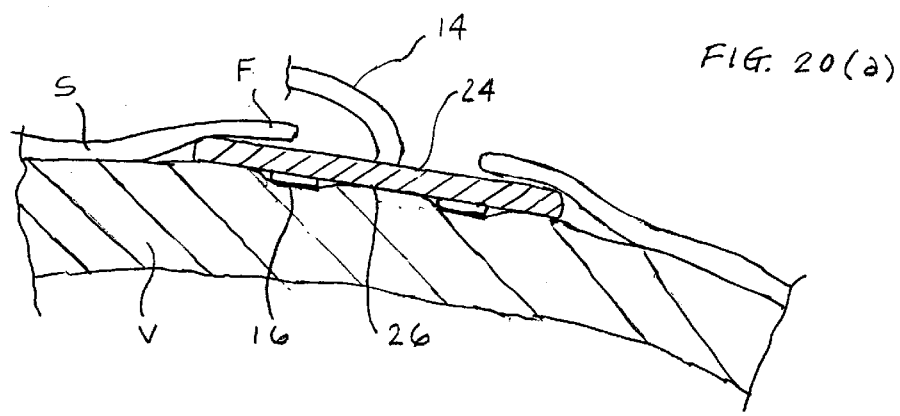
FIG. 20(a) is a sectional view illustrating a stage in the embodiment of FIG. 19.
Figure 20B:
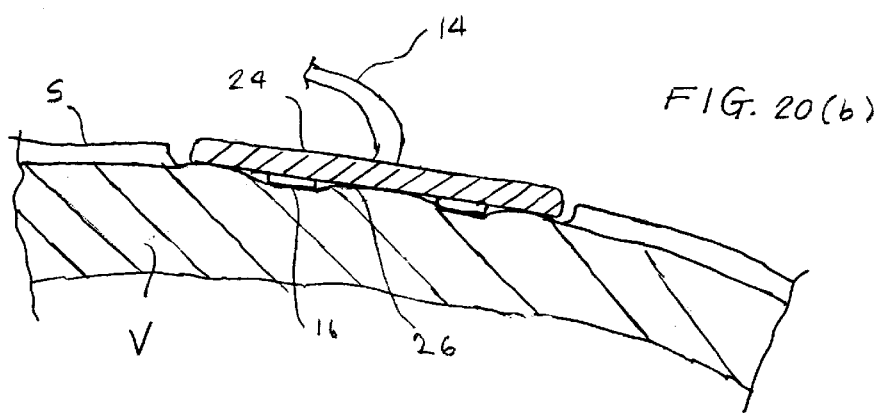
FIG. 20(b) is a sectional view similar to FIG. 20(a), illustrating another alternative embodiment in accordance with the invention.

FIGS. 19–20 illustrate an alternative procedure for installing the patch 24 in accordance with the invention. (The procedure is applicable to embodiments 124, 224, 324, 424, 524, and 724, described above.) Under certain operative conditions, it may be indicated that the serosa S, a thin membrane forming the outer surface of the viscera V, should be partially removed prior to placement of the patch 24. As illustrated in FIG. 19, the installation of patch 24 may include an additional step of forming an incision I in the serosa S with a cutting instrument, such as scalpel apparatus 690 or similar device. Surgical instruments, such as endoscopic grasping instrument 670 or a blunt dissection instrument (not shown), may be used to dissect the serosa S from the adjoining tissue.

As illustrated in FIGS. 19 and 20, the distal surface 26 of patch 24 may then be placed on a surface of the viscera V beneath the serosa S. According to a preferred embodiment, patch 24 may be installed beneath a flap portion F of the serosa, as illustrated in FIG. 20(*a*). Alternatively, a portion of the serosa S may be removed from the viscera V when the distal surface 26 is placed on the viscera, as illustrated in FIG. 20(*b*). Subsequently, the patch 24 may be attached to the viscera V with staples or sutures, as described above with respect to FIGS. 16–17. Patch 24 may alternatively be attached with the helical attachment member 650 (FIG. 18).

Figure 21:
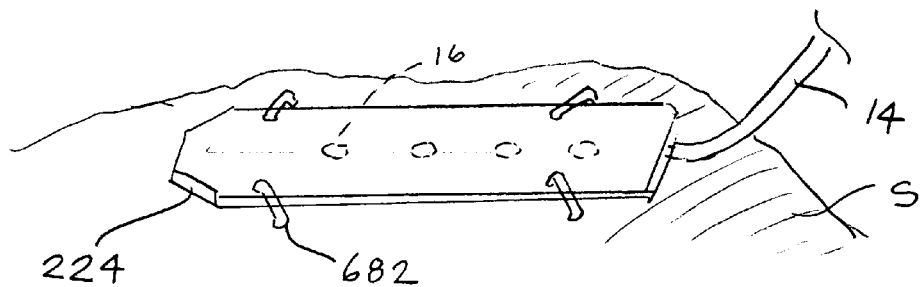
FIG. 21 is a view similar to FIG. 16, illustrating the alternative embodiment of FIG. 5 in accordance with the invention.

FIG. 21 illustrates elongated patch 224 attached to the viscera V with staples or sutures 682, in a substantially similar manner as described with respect to FIGS. 16–17 for patch 24. Alternatively, a suturing apparatus, such as a suture needle (not shown), may be used to suture any of the above patch configurations to the viscera.

Figure 22:
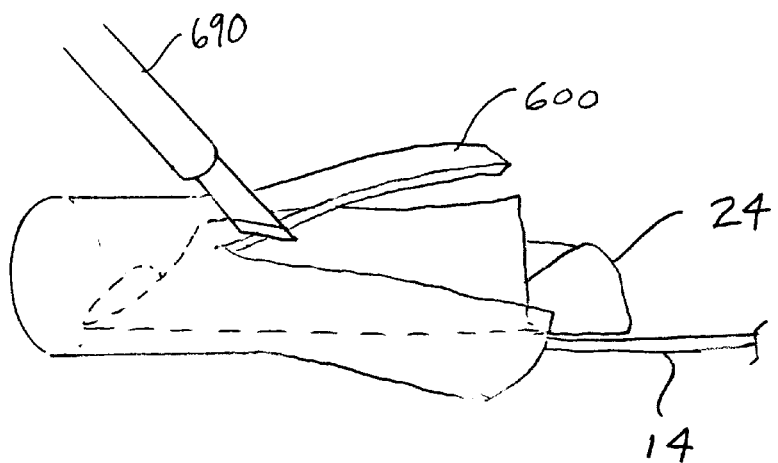
FIG. 22 is a view similar to FIG. 15, illustrating an alternative step in the process of FIGS. 14–17 in accordance with the invention.

According to an alternative embodiment, the patch 24 may be released from the sleeve 600 by mechanical separation of the sleeve 600. As illustrated in FIG. 22, surgical apparatus, such as scalpel apparatus 690, may be used to cut or tear the sleeve 600 longitudinally.

Figure 23:
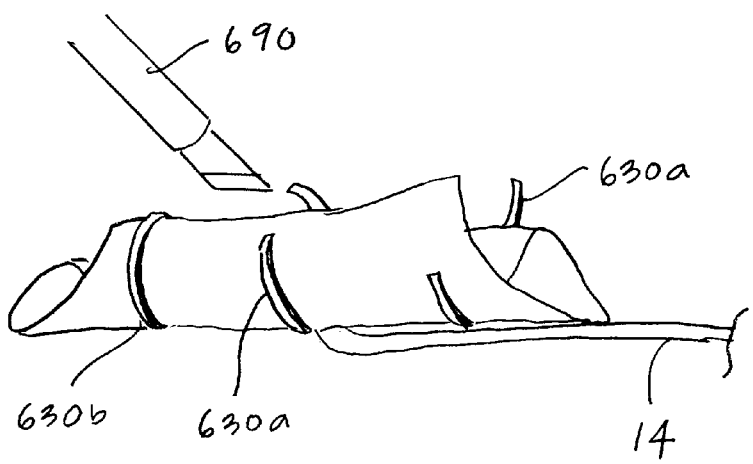
FIG. 23 is a view similar to FIG. 15, illustrating another alternative step in the process of FIGS. 14–17 in accordance with the invention.

According to another alternative embodiment, the patch 24 is maintained in the compact configuration as illustrated in FIG. 13, above, and secured by bands 630. As illustrated in FIG. 23, the bands 630 are severed by tearing or cutting, for example, by use of surgical instrumentation, such as apparatus 690. In the FIG., bands 630*a* have already been severed, and band 630*b* is currently secured around patch 24. A further step in the process in accordance with the invention may be to sever band 630*b* to entirely release patch 24 to its open, uncompacted configuration. (See, e.g., FIGS. 2 and 16).

The foregoing is merely illustrative of the principles of this invention and various modifications can be made by those skilled in the art without departing from the scope and spirit of the invention.

What is claimed is:

1. An apparatus for stimulating neuromuscular tissue of the viscera of a patient by applying electrical pulses to the neuromuscular tissue, the electrical pulses supplied by a pulse generator, comprising:

at least two electrodes configured for electrical connection with the pulse generator;

an electrode attachment member having a distal surface configured for attachment to a surface of the neuromuscular tissue to be stimulated, wherein the electrode attachment member supports the electrodes adjacent the distal surface thereof to provide an interface between the electrodes and the surface of the neuromuscular tissue to be stimulated when attached to the surface, wherein the distal surface of the electrode attachment member is flexible and has a first configuration which is substantially flat so as to substantially conform to the surface of the neuromuscular tissue to be stimulated when attached to the surface, wherein the distal surface of the electrode attachment member has a second configuration which is substantially cylindrically shaped and reduced in size relative to the first configuration so as to inserted into the patient through a minimally invasive laparoscopic access opening, and wherein the distal surface of the electrode attachment member may be returned to the first configuration once inserted into the patient in order to be attached to the surface of the neuromuscular tissue to be stimulated; and an annular means for receiving the electrode attachment member in the second configuration and for maintaining the electrode attachment member in the second configuration until after insertion into the patient through the minimally invasive laparoscopic access opening.

2. Apparatus defined in claim 1, wherein the interface between the electrodes and the surface of the neuromuscular tissue is sufficient to allow for low impedance stimulation of the neuromuscular tissue by the pulse generator.

3. Apparatus defined in claim 1, wherein the electrode attachment member is configured to receive staples therethrough for attachment to the surface of the neuromuscular tissue.

4. Apparatus defined in claim 1, wherein the electrode attachment member is configured to receive sutures therethrough for attachment to the surface of the neuromuscular tissue.

5. Apparatus defined in claim 1, wherein the annular means comprises a band configured to surround the electrode attachment member in the second configuration.

6. Apparatus defined in claim 1, wherein the electrode attachment member is long and narrow.

7. Apparatus defined in claim 1, wherein the electrode attachment member has a substantially circular distal surface with a center and the electrodes are substantially equidistantly spaced about the center of the distal surface.

8. Apparatus defined in claim 1, wherein the viscera includes the gastrointestinal tract.

9. Apparatus defined in claim 1, wherein the electrode attachment member has a substantially helical attachment member protruding from the distal surface thereof for attachment to the neuromuscular tissue.

10. Apparatus defined in claim 9, wherein the substantially helical attachment member also functions as one of the electrodes.

* * * * *